US011103497B2

(12) United States Patent
Hewes

(10) Patent No.: US 11,103,497 B2
(45) Date of Patent: Aug. 31, 2021

(54) TREATMENT OF IMATINIB RESISTANT LEUKEMIA

(75) Inventor: Becker Hewes, Middlesex, MA (US)

(73) Assignee: Wyeth LLC, New York, NY (US)

( * ) Notice: Subject to any disclaimer, the term of this patent is extended or adjusted under 35 U.S.C. 154(b) by 2100 days.

(21) Appl. No.: 12/129,935

(22) Filed: May 30, 2008

(65) Prior Publication Data

US 2008/0318971 A1 Dec. 25, 2008

Related U.S. Application Data

(60) Provisional application No. 60/932,650, filed on Jun. 1, 2007.

(51) Int. Cl.
*A61K 31/4709* (2006.01)
*A61K 31/496* (2006.01)

(52) U.S. Cl.
CPC ........ *A61K 31/4709* (2013.01); *A61K 31/496* (2013.01)

(58) Field of Classification Search
CPC .................................................. A61K 31/4709
USPC ......................................................... 514/183
See application file for complete search history.

(56) References Cited

U.S. PATENT DOCUMENTS

| 6,002,008 | A | 12/1999 | Wissner et al. |
| 6,297,258 | B1 | 10/2001 | Wissner et al. |
| 6,780,996 | B2 | 8/2004 | Boschelli et al. |
| 7,417,148 | B2 | 8/2008 | Boschelli et al. |
| 2003/0212276 | A1 | 11/2003 | Boschelli et al. |
| 2005/0101780 | A1 | 5/2005 | Boschelli et al. |
| 2006/0263354 | A1 | 11/2006 | Chin et al. |

FOREIGN PATENT DOCUMENTS

| WO | 2003031608 A2 | 4/2003 |
| WO | WO 2006/124863 A | 11/2006 |
| WO | 2007/044411 A2 | 4/2007 |
| WO | 2007056177 A2 | 5/2007 |
| WO | 2008/150957 A2 | 12/2008 |

OTHER PUBLICATIONS

Gorre, M. E. et al., *Clinical Resistance to STI-571 Cancer Therapy Caused by BCR-ABL Gene Mutation or Amplification*, Science 2001, 293(5531):876-880.
Le Coutre, P. et al., *Induction of resistance to the Abelson inhibitor STI571 in human leukemic cells through gene amplification*, Blood 2000, 95(5):1758-66.
Talpaz et al., *Dasatinib in Imatinib-Resistant Philadelphia Chromosome-Positive Leukemias.*, N. Eng. J. Med. 2006, 354:2531-2541.
Branford et al., *Detection of BCR-ABL mutations in patients with CML treated with imatinib is virtually always accompanied by clinical resistance, and mutations in the ATP phosphate-binding loop (P-loop) are associated with a poor prognosis*, Blood Jul. 1, 2003, vol. 102, No. 1, pp. 276-283.
Soverini et al., *Presence or the Emergence of a F317L BCR-ABL Mutation May be Associated With Resistance to Dasatinib in Philadelphia Chromosome-Positive Leukemia*, J. Clin. Oncol. Nov. 20, 2006, 24(33):e51-2.
Puttini et al., *In vitro and In vivo Activity of SKI-606, a Novel Src-Abl Inhibitor, against Imatinib-Resistant Bcr-Abl+ Neoplastic Cells*, Cancer Res. 2006, 66(23): Dec. 1, 2006.
Boschelli, D. H., et al., *Optimization of 4-Phenylamino-3-quinolinecarbonitriles as Potent Inhibitors of Src Kinase Activity*, J. Med. Chem. 2001, 44: 3965-3977.
Boschelli, D. H., et al., *Synthesis and Src Kinase Inhibitory Activity of a Series of 4-Phenylamino-3-quinolinecarbonitriles*. J. Med. Chem. 2001, 44: 822-833.
Boschelli, D. H., et al., *Investigation of the Effect of Varying the 4-Anilino and 7-Alkoxy Groups of 3-Quinolinecarbonitriles on the Inhibition of Src Kinase Activity*, Bioorg. Med. Chem. Lett. 2003, 13:3797-3800.
Boschelli, D. H., et al., *7-Alkoxy-4-phenylamino-3-quinolinecarbonitriles as Dual Inhibitors of Src and Abl Kinases*, J. Med. Chem. 2004, 47:1599-1601.
Ye, F. et al., 221st National Meeting of the American Chemical Society, San Diego, Calif. (Apr. 2001) (Abstract Only).
Jabbour, E. et al., *New Targeted Therapies for Chronic Myelogenous Leukemia: Opportunities to Overcome Imatinib Resistance*. Seminars in Hematology, Philadelphia, PA (Jan. 2007).
Gumireddy, K. et al., *A non-ATP-competitive inhibitor of BCL-ABL overrides imatinib resistance*. Proceedings of the National Academy of Sciences of the USA 6, 1992-1997 (2005).
Jabbour, E. et al., *Current and Emerging Treatment Options in Chronic Myeloid Leukemia*. American Cancer Society (2007) 11, 2171-2181.
Golas, J. M. et al., Cancer Res. *SKI-606, a 4-Anilino-3-quinolinecarbonitrile Dual Inhibitor of Src and Abl Kinases, Is a Potent Antiproliferative Agent against Chronic Myelogenous Leukemia Cells in Culture and Causes Regression of K562 Xenografts in Nude Mice*. 63:2, 375-381 (2003).
Hochhaus et al., *Imatinib therapy in chronic myelogenous leukemia: strategies to avoid and overcome resistance*. Leukemia (2004) 18, 1321-1331.
Drucker, B. et al., *Circumventing Resistance to Kinase-Inhibitor Therapy*. N. Engl. J. Med. Jun. 15, 2006; 354(24):2594-6.
Shah, N. P. et al., *Multiple BCR-ABL kinase domain mutations confer polyclonal resistance to the tyrosine kinase inhibitor imatinib (STI571) in chronic phase and blast crisis chronic myeloid leukemia*. Cancer Cell, vol. 2. (2), Aug. 2002, pp. 117-125.
Kantarjian, H. et al., *Nilotinib in Imatinib-Resistant CML and Philadelphia Chromosome-Positive ALL*, N. Engl. J. Med. Jun. 15, 2006; 354(24):2542-2551.
Annex to Form PCT/ISA/206, Jan. 13, 2009.
Cortes, J. et al., "Efficacy and Safety of Bosutinib (SKI-606) among Patients with Chronic Phase Ph+ Chronic Myelogenous Leukemia (CML)," 2007, Blood, vol. 110, pp. 225A.

(Continued)

*Primary Examiner* — Yong S. Chong
(74) *Attorney, Agent, or Firm* — Corey Williams

(57) ABSTRACT

The present invention provides 4-anilino-3-quinolinecarbonitriles compounds useful for treating a subject having an BcrAbl positive leukemia that is resistant to imatinib.

10 Claims, 2 Drawing Sheets

(56) References Cited

OTHER PUBLICATIONS

Cortes, Jorge, et al., "A Phase 1/2 Study of SKI-606, a Dual Inhibitor of Src and Abl Kinases, in Adult Patients with Philadelphia Chromosome Positive (Ph+) Chronic Myelogenous Leukemia (CML) or Acute Lymphocytic Leukemia (ALL) Relapsed, Refractory or Intolerant of Imatinib.," 2006, Blood, vol. 108, No. 11, p. 54A.
Jabbour, Elias et al., "New Targeted Therapies for Chronic Myelogenous Leukemia: Opportunities to Overcome Imatinib Resistance," 2007, Seminars in Hematology, vol. 44, pp. S25-S31.
Puttini, Miriam et al., "In Vitro and In Vivo Activity of SKI-606, a Novel Abl/Src Inhibitor, Against Imatinib Resistant BCR-ABL+ Neoplastic Cells," 2006, Blood, vol. 108, No. 11, p. 617A.
Blasdel, Carolyn et al., "Therapeutic Drug Monitoring of Imatinib and Impact on Clinical Decision Making," 2006, Blood, vol. 108, p. 290B.
Grafone, Tiziana et al., "A Novel 4-anilino-3-quinolinecarbonitrile Dual Src and Abl Kinase Inhibitor (SKI-606) Has In Vitro Activity on CML Ph+Blast Cells Resistant to Imatinib.," 2004, Blood, vol. 104, pp. 549A-550A.
O'Hare, Thomas et al., "Bcr-Abl Kinase Domain Mutations and the Unsettled Problem of Bcr-Abl[315l]: Looking into the Future of Controlling Drug Resistance in Chronic Myeloid Leukemia," 2007, Clinical Lymphoma and Myeloma, vol. 7, pp. S120-S130.
Swords, Ronan et al., "Novel Abl Kinase Inhibitors in Chronic Myeloid Leukemia in Blastic Phase and Philadelphia Chromosome-Positive Acute Lymphoblastic Leukemia," 2007, Clinical Lymphoma and Myeloma, vol. 7, pp. S113-S119.
Shah, Neil P., "Improving upon the promise of targeted therapy of human malignancy: Chronic myeloid leukemia as a paradigm," 2006, Cancer Chemotherapy and Pharmacology, vol. 58, pp. s49-s53.
Weisberg, Ellen et al., "Second generation inhibitors of BCR-ABL for the treatment of imatinib-resistant chronic myeloid leukaemia," 2007, Nature Reviews Cancer, vol. 7, pp. 345-356.
Kantarjian, Hagop M. et al., "Important Therapeutic Targets in Chronic Myelogenous Leukemia," 2007, Clinical Cancer Research, vol. 13, pp. 1089-1097.
Tauchi, Tetsuzo and Ohyashiki, Kazuma, "The Second Generation of BCR-ABL Tyrosine Kinase Inhibitors," 2006, International Journal of Hematology, vol. 83, pp. 294-300.
Manley, Paul William et al., "Advances in the structural biology, design and clinical development of Bcr-Abl kinase inhibitors for the treatment of chronic myeloid leukaemia," 2005, Biochimica et Biophysica Acta, vol. 1754, pp. 3-13.
Martinelli, Giovanni et al., "New tyrosine kinase inhibitors in chronic myeloid leukemia," 2005, Haematologica, vol. 90, pp. 534-541.
Nardi, Valentina et al., "Mechanisms and implications of imatinib resistance mutations in BCR-ABL," 2004, Current Opinion in Hematology, vol. 11, pp. 35-43.
Gambacorti-Passerini. C. et al., "Bosutinib (SKI-606) Demonstrates Clinical Activity and is Well Tolerated in Patients with AP and BP CML and Ph+ ALL," Dec. 6-9, 2008, American Society of Hematology.
Cortes, J. et al., "Efficacy and Safety of Bosutinib (SLI-606) in Patients with Chronic Phase (CP) Ph+ Chronic Myeloid Leukemia (CML) with Resistance or Intolerance to Imatinib," Dec. 6-9, 2008, American Society of Hematology.
Redaelli, Sara et al., "Activity of Bosutinib, Dasatinib, and Nilotinib Against 18 Imatinib-Resistant BCR/ABL Mutants," Journal of Clinical Oncology, vol. 27, Published Ahead of Print on Dec. 15, 2008 as 10.1200/JCO.2008.19.8853.
Gambacorti-Passerini. C. et al., "Bosutinib (SKI-606) Demonstrates Clinical Activity and is Well Tolerated Among Patients with AP and BP CML and Ph+ ALL," 2007, Presentation.
Skaggs et al., "Phosphorylation of the ATP-binding loop directs oncogenicity of drug-resistant BCR-ABL mutants", PNAS, 103(51), 19466-19471, 2006.
Shah et al., "Mechanisms of resistance to STI571 in Philadelphia chromosome-associated leukemias", Oncogene, 22, 7389-7395, 2003.
Cortes et al., "Dynamics of BCR-ABL kinase domain mutations in chrnic myeloid leukemia after sequential treatment with multiple tyrosine kinase inhibitors", Blood, 110, 4005-4011, 2007.
Quintas-Cardama et al., "Tailoring tyrosine kinase inhibitor therapy to tackle specific BCR-ABL1 mutant clones", Leukemia Research, 32, 1313-1316, 2008.
Anand, et al., "Varying response to escalating the dose of imatinib in patients with CML who "acquire" a BCR-ABLM244v mutant allele," Blood, 2006, 2881-2882, vol. 108, No. 8.
Belikov, V. G. (1993). Farmatsevticheskayaya Himiya (2nd ed., vol. 1., pp. 43-47). M., Vysschaya Shkola. English Translation Provided.
Corbin, et al., "Several Bcr-Abl kinase domain mutants associated with imatinib mesylate resistance remain sensitive to imatinib," Blood, 2003, 4611-4614, vol. 101, No. 11.
Valent, "Imatinib-resistant chronic myeloid leukemia (CML): Current concepts on pathogenesis and new emerging pharmacologic approaches," Biologies: Targets & Therapy, 2007, 433-448, vol. 1, No. 4.

RESPONSE TO THERAPY: PATIENTS WITH NO PRIOR DRUG EXPOSURE*

| RESPONSE | CHRONIC CML N (%) | ADVANCED N (%) |
|---|---|---|
| HEMATOLOGIC RESPONSE | | |
| EVALUABLE | 36 | 9 |
| CHR | 33 (92) | 7 (78) |
| CHR+NEL+MR | 33 (92) | 8 (89) |
| CYTOGENETIC RESPONSE | | |
| EVALUABLE[†] | 31 | 5 |
| COMPLETE | 10 (32) | 1 (17) |
| PARTIAL | 3 (10) | 2 (40) |
| MAJOR | 13 (42) | 3 (60) |

*PATIENTS HAD NO PRIOR EXPOSURE TO KINASE INHIBITORS OTHER THAN IMATINIB.
[†]PATIENTS EVALUABLE FOR MAJOR OR COMPLETE CYTOGENIC RESPONSE (ie, BASELINE CYTOGENETIC RESPONSE OF PARTIAL RESPONSE OR WORSE AND ≥1 POST-BASELINE ASSESSMENT OF CYTOGENETIC RESPONSE).

FIG. 1

TREATMENT OF IMATINIB RESISTANT LEUKEMIA

CROSS-REFERENCE TO RELATED APPLICATIONS

This application claims priority from U.S. Provisional Application No. 60/932,650, filed Jun. 1, 2007, which is incorporated by reference in its entirety.

FIELD OF THE INVENTION

The invention is directed to methods of treatment of drug-resistant cancer. In particular, the invention is directed to methods of treating imatinib-resistant BcrAbl positive leukemia.

BACKGROUND OF THE INVENTION

Imatinib, which is sold under the trade names Gleevac and Glivec, has arguably transformed the treatment of chronic myeloid leukemia by helping many patients achieve a nearly 90% 5-year survival rate. A subset of patients on imatinib, which is sold under the trade names Gleevac and Glivec, develop resistance to the drug, often because of bcrabl mutations in the tyrosine kinase. Treatment with imatinib has allowed patients with chronic myelogenous leukemia (CML) to experience a nearly 90 percent five-year survival rate, as the drug blocks the tyrosine kinase protein "BcrAbl," an abnormal protein driving the overproduction of abnormal white blood cells characteristic of leukemia. However, many patients have eventually developed resistance to this treatment because their cancer cells are able to mutate and adapt, causing their disease to relapse.

The aberrantly activated tyrosine kinase BcrAbl (the product of bcrabl gene and the Philadelphia Chromosome) is causally associated with Chronic Myelogenous Leukemia and Acute lymphocytic leukemia. Constitutive tyrosine kinase activity of BcrAbl promotes proliferation and survival of chronic myelogenous leukemia (CML) cells. Inhibition of BcrAbl tyrosine kinase activity or signaling proteins activated by BcrAbl in CML cells blocks proliferation and causes apoptotic cell death. The selective Abl kinase inhibitor, STI-571 (marketed as Gleevec), is toxic to CML cells in culture, causes regression of CML tumors in nude mice, and is currently used to treat CML patients. Expression of BcrAbl in hematopoietic stem cells promotes transformation and acts early in leukemogenesis. Inhibition of this kinase with STI-571 effectively controls CML in the chronic phase of the disease but more advanced patients frequently progress on STI-571 therapy. In vitro models of STI-571 resistance and clinical specimens from resistant patients demonstrated that overexpression of other kinases or activation of distinct signaling pathways is associated with BcrAbl independence. Inhibition of the tyrosine kinase activity of BcrAbl is an effective strategy for targeting CML as demonstrated by the clinical efficacy of STI-571. Other molecules, including Src family kinases, play a role in downstream signaling from BcrAbl, and as such, are potential therapeutic targets for the treatment of STI-571-resistant disease. Src family kinases including Lyn and Hck have been implicated in downstream signaling from BcrAbl.

Although the selective Abl kinase inhibitor STI-571 is efficacious and well tolerated by most patients in chronic-stage CML, patients in accelerated and blast crises stages of the disease tend to be less responsive. Consequently, there is a need for alternative agents that are effective in late-stage disease. The frequency of bcr/abl mutations in CML resistant patients has increased to 90% (Hochhaus et al. Leukemia 2004)) from 42% Cancer Cell, Vol 2. (2), August 2002, Pages 117-125.Imatinib is approved as a first line therapy for the newly diagnosed CML patients. However resistance to imatinib due to point mutations in the bcr/abl gene is being recognized as a hurdle in the therapy of CML patients. Gore, Science 2001; 293(5531):876-880 and Lecoutre, Blood 2000; 95(5):1758-66.

Kantarijian et al. have demonstrated that nilotinob is not effective against CML when patients have the amino acid mutation in BcrAbl T315I N Engl J. Med. 2006 Jun. 15; 354(24):2594-6.

Talpaz et al. have shown that Dasatinib in Imatinib-Resistant Philadelphia Chromosome-Positive Leukemias (New England J. Med. 2006:354:2531-2541) also has no effect against the T315I mutation. This reference also demonstrated that Dasatinib can cause hematologic toxicity and edema.

Branford et al. reported that BcrAbl mutations in patients with CML treated with imatinib are virtually always accompanied by clinical resistance, and mutations in the ATP phosphate-binding loop (P-loop) are associated with a poor prognosis. Blood, 1 Jul. 2003, Vol. 102, No. 1, pp. 276-283.

U.S. Pat. No. 6,297,258 discloses substituted 3-cyanoquinolines that are useful as antineoplastic agents and in the treatment of polycystic kidney disease. U.S. Patent Application No. 20050101780 discloses methods of treating preventing or inhibiting CML by providing to a subject a therapeutically effective amount of SKI-606.

U.S. Patent Publication No. 20050101780 specifically discloses the use of a compound having the structural formula

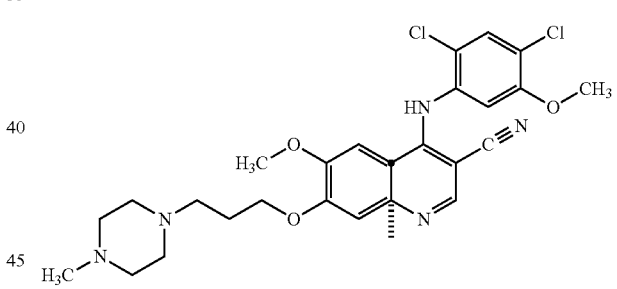

for the treatment of CML. This compound is also known as bosutinib or SKI-606 and has the chemical name 4-[(2,4-Dichloro-5-methoxy-phenyl)amino]-6-methoxy-7-[3-(4-methyl-1-piperazinyl)propoxy]-3-quinolinecarbonitrile Soverini et al. demonstrated the resistance to dasatinib of patients with F317V., J Clin Oncol. 2006 Nov. 20; 24(33): e51-2.

Puttini et al. have shown that SKI-606, a novel Src-Abl inhibitor is effective at reducing replication of imatininb resistant CML cell lines having certain mutations associate with imatinib resistance. Cancer Res. 2006; 66(23):Dec. 1, 2006.

SUMMARY OF THE INVENTION

It has been discovered that a significant number of imatinib resistant patients respond favorably to treatment with SKI-606 (4-[(2,4-Dichloro-5-methoxy-phenyl)amino]-6-methoxy-7-[3-(4-methyl-1-piperazinyl)propoxy]-3-quinolinecarbonitrile).

It has also been discovered that a significant number of patients having known point mutations associated with resistance to imatinib respond favorably to treatment with SK-606. Thus, in one embodiment, the invention provides a method of treating a subject suffering from BcrAbl positive leukemia, wherein the leukemia is resistant to treatment with imatinib, the method comprising administering to the subject a therapeutically effective amount of a compound of the Formula:

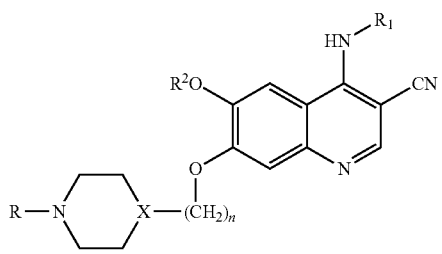

wherein:
n is 1, 2 or 3;
X is N or CH, provided that when X is N, then n is 2 or 3;
R is alkyl of from 1 to 3 carbon atoms;
R¹ is selected from the group consisting of 2,4-dichloro-5-methoxyphenyl; 2,4-dichlorophenyl; 3,4,5-trimethoxyphenyl; 2-chloro-5-methoxyphenyl; 2-methyl-5-methoxyphenyl; 2,4-dimethylphenyl; 2,4-dimethyl-5-methoxyphenyl; and 2,4-dichloro-5-ethoxyphenyl; and
R² is alkyl of from 1 to 2 carbon atoms;
or a pharmaceutically acceptable salt thereof.

In one embodiment, the method comprises treating a subject suffering from Leukemia and in some embodiments the Leukemia is selected from CML and Acute Lymphocytic Leukemia (AML).

In some embodiments, the invention provides a method of treatment wherein the imatinib resistant subjects have one or more nucleic acid mutations in the bcrabl gene selected from the group consisting of: 1052T>C; 1075T>G; 1187A>C; 1295T>C; 1457T>C; 730A>G; 742C>S; 749G>A; 757T>C; 758A>T; 763G>A; 787A>G; 817T>A; 944C>T; 944C>T; 949T>C; and 992A>G.

In some embodiments, the invention provides a method of treatment wherein the imatinib resistant subjects have one or more amino acid mutations in BcrAbl selected from the group consisting of: M351T; F359V; H396P; I432T; F486S; M244V; L248V; G250E; Y253H; Y253F; E255K; K263E; L273M; T315I; F317L; and N331S.

In one embodiment, the compositions of the present invention are administered at a concentration selected from about 100 and about 1000 mg, between about 200 and about 800 mg, between about 300 and about 700 mg, between about 400 and about 600 mg and any intervals or fractions included within these ranges. In one embodiment, the compounds are administered at a concentration between 400 and 600 mg per day. In one embodiment, the compounds are administered at a concentration at about 500 mg per day.

In another embodiment, the invention provides a method of treating a subject suffering from BcrAbl positive leukemia, wherein the leukemia is resistant to treatment with imatinib, the method comprising administering to the subject a therapeutically effective amount of a compound of the Formula:

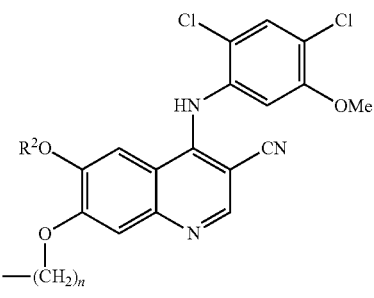

wherein:
X is N or CH;
n is 3;
R² and R are methyl;
or a pharmaceutically acceptable salt thereof.

In another embodiment, the invention provides a method of treating a subject suffering from BcrAbl positive leukemia, wherein the leukemia is resistant to treatment with imatinib, the method comprising administering to the subject a therapeutically effective amount of a compound of the Formula:

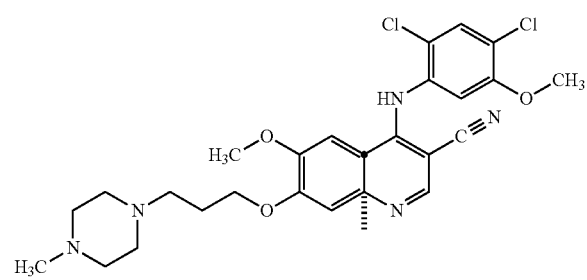

In another embodiment, the invention provides the use of a compound of the Formula:

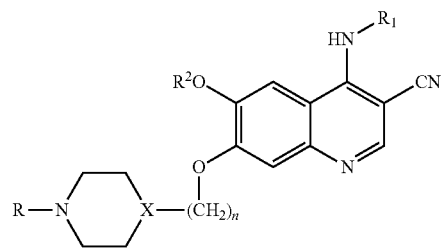

wherein:
n is 1, 2 or 3;
X is N or CH, provided that when X is N, then n is 2 or 3;
R is alkyl of from 1 to 3 carbon atoms;
R¹ is selected from the group consisting of 2,4-dichloro-5-methoxyphenyl; 2,4-dichlorophenyl; 3,4,5-trimethoxyphenyl; 2-chloro-5-methoxyphenyl; 2-methyl-5-methoxyphenyl; 2,4-dimethylphenyl; 2,4-dimethyl-5-methoxyphenyl; and 2,4-dichloro-5-ethoxyphenyl; and
R² is alkyl of from 1 to 2 carbon atoms;
or a pharmaceutically acceptable salt thereof;
for use in the manufacture of a medicament for the treatment of imatinib resistant cancer.

In another embodiment, the invention provides the use of a composition encompassed by the formula

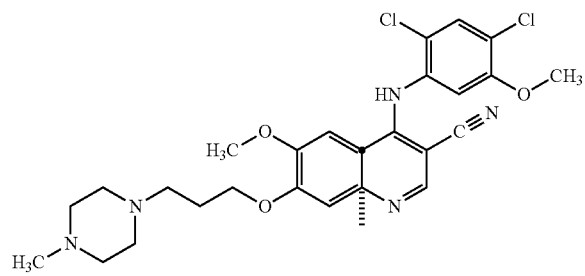

or a pharmaceutically acceptable salt thereof;
for use in the manufacture of a medicament for the treatment of imatinib resistant leukemia. The composition is also known as SKI-606 and bosutinib and has the chemical name 4-[(2,4-Dichloro-5-methoxy-phenyl)amino]-6-methoxy-7-[3-(4-methyl-1-piperazinyl)propoxy]-3-quinolinecarbonitrile.

BRIEF DESCRIPTION OF THE DRAWINGS

FIG. 1 shows a summary of responses hematological and cytogenetic responses following treatment with SKI-606.

DETAILED DESCRIPTION OF THE INVENTION

General Methods

Figure 2:
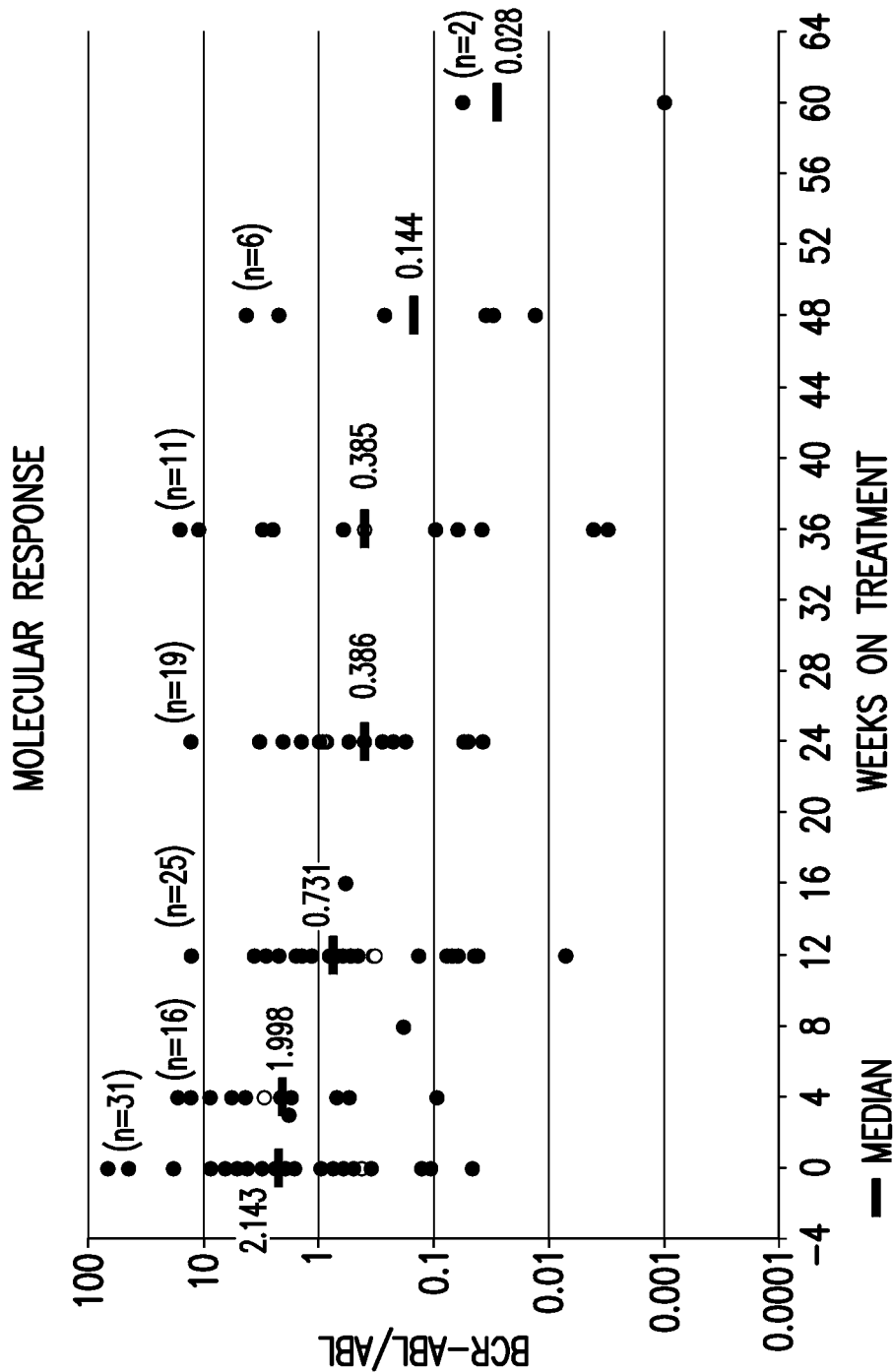
FIG. 2 shows levels of expression of bcrabl gene.

Automated complete blood counts, differential counts (with manual confirmation of abnormalities), bone marrow morphology, and cytogenetics are used to determine response to treatment.

Bone marrow morphology is used to determine the blast and immature myeloid cell counts in order to define disease phases.

Standard cytogenetics are used to determine the presence of the Philadelphia chromosome and its percent presence in marrow. Twenty or more metaphases should be counted for this determination. FISH (Fluorescent in situ hybridization) analysis may be used to confirm presence of BcrAbl fusion product.

Reverse Transcriptase Polymerase Chain Reaction (RT-PCR) for BcrAbl copy number is performed on peripheral blood.

As used herein the term "BcrAbl positive leukemia" refers to a leukemia that is associated with expression of the bcrabl gene.

Cytogenetic response to treatment. As used herein, a "cytogenetic response to treatment" indicates a relative disappearance of the Philadelphia chromosome in treated subjects as determined by a percentage of Philadelphia chromosome positive cells present. The response can be minimal, minor, partial or complete. A "negative" cytogenetic response represents approximately 95.5% cells positive for the Philadelphia chromosome after treatment. A "minimal response" indicates approximately 66-95% cells positive for the Philadelphia chromosome. A "minor" cytogenetic response indicates 36-65% cells positive for the Philadelphia chromosome. A "partial" response indicates 1-35% cells positive for the PC. complete response indicates 0% cells positive for the Philadelphia chromosome. These figures for % positive are based on analysis of 20 metaphases (per subject?). A fluorescence in situ hybridization (FISH)-based assay can be used to qualify response if insufficient metaphases are available.

Hematologic Responses to treatment. As used herein, a "hematologic response to treatment" indicates the elimination of microscopically observed leukemia cells in the blood.

The compounds of this invention may be used for treating, preventing, or inhibiting imatinib resistant leukemia. In a preferred embodiment the compounds are used as part of a pharmaceutical composition.

Pharmaceutically acceptable salts are those derived from such organic and inorganic acids as: acetic, lactic, carboxylic, citric, cinnamic, tartaric, succinic, fumaric, maleic, malonic, mandelic, malic, oxalic, propionic, hydrochloric, hydrobromic, phosphoric, nitric, sulfuric, glycolic, pyruvic, methanesulfonic, ethanesulfonic, toluenesulfonic, salicylic, benzoic, and similarly known acceptable acids.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. In a preferred embodiment, a straight chain or branched chain alkyl has 3 or fewer carbon atoms in its backbone.

Compounds may be provided orally, by intralesional, intraperitoneal, intramuscular or intravenous injection; infusion; liposome-mediated delivery; topical, nasal, anal, vaginal, sublingual, uretheral, transdermal, intrathecal, ocular or otic delivery. In order to obtain consistency in providing the compound of this invention it is preferred that a compound of the invention is in the form of a unit dose.

Suitable unit dose forms include tablets, capsules and powders in sachets or vials. Such unit dose forms may contain from 0.1 to 1000 mg of a compound described herein to treat imatinib resistant leukemia and preferably from 400 to 600 mg. In another embodiment the unit dosage forms contain 500 mg of a compound of the present invention.

In one embodiment, the daily dosage is between 400 and 600 mg per day. In yet another embodiment, the compounds can be administered in unit dosage forms containing 500 mg.

The compounds of the present invention can be administered orally. Such compounds may be administered from 1 to 6 times a day, more usually from 1 to 4 times a day. The effective amount will be known to one of skill in the art; it will also be dependent upon the form of the compound. One of skill in the art could routinely perform empirical activity tests to determine the bioactivity of the compound in bioassays and thus determine what dosage to administer.

The compounds of the invention may be formulated with conventional excipients, such as a filler, a disintegrating agent, a binder, a lubricant, a flavoring agent, a color additive, or a carrier. The carrier may be for example a diluent, an aerosol, a topical carrier, an aqueous solution, a nonaqueous solution or a solid carrier. The carrier may be a polymer or a toothpaste. A carrier in this invention encompasses any of the standard pharmaceutically accepted carriers, such as phosphate buffered saline solution, acetate buffered saline solution, water, emulsions such as an oil/water emulsion or a triglyceride emulsion, various types of wetting agents, tablets, coated tablets and capsules.

When provided orally or topically, such compounds would be provided to a subject by delivery in different carriers. Typically, such carriers contain excipients such as starch, milk, sugar, certain types of clay, gelatin, stearic acid, talc, vegetable fats or oils, gums, or glycols. The specific carrier would need to be selected based upon the desired method of delivery, for example, phosphate buffered saline (PBS) could be used for intravenous or systemic delivery and vegetable fats, creams, salves, ointments or gels may be used for topical delivery.

The compounds of the present invention may be delivered together with suitable diluents, preservatives, solubilizers, emulsifiers, adjuvants and/or carriers useful in treatment or prevention of neoplasm. Such compositions are liquids or lyophilized or otherwise dried formulations and include diluents of various buffer content (for example, Tris-HCl, acetate, phosphate), pH and ionic strength, additives such as albumins or gelatin to prevent absorption to surfaces, detergents (for example, TWEEN 20, TWEEN 80, PLURONIC F68, bile acid salts), solubilizing agents (for example, glycerol, polyethylene glycerol), anti-oxidants (for example ascorbic acid, sodium metabisulfate), preservatives (for example, thimerosal, benzyl alcohol, parabens), bulking substances or tonicity modifiers (for example, lactose, mannitol), covalent attachment of polymers such as polyethylene glycol, complexation with metal ions, or incorporation of the compound into or onto particulate preparations of hydrogels or liposomes, micro-emulsions, micelles, unilamellar or multilamellar vesicles, erythrocyte ghosts, or spheroblasts. Such compositions will influence the physical state, solubility, stability, rate of in vivo release, and rate of in vivo clearance of the compound or composition. The choice of compositions will depend on the physical and chemical properties of the compound capable of treating or preventing a neoplasm.

The compound of the present invention may be delivered locally via a capsule that allows a sustained release of the compound over a period of time. Controlled or sustained release compositions include formulation in lipophilic depots (for example, fatty acids, waxes, oils).

The present invention further provides a compound of the invention for use as an active therapeutic substance for treating, preventing, or inhibiting CML.

The present invention further provides a method of treating CML in humans, which comprises administering to the infected individual an effective amount of a compound or a pharmaceutical composition of the invention. The dose provided to a patient will vary depending upon what is being administered, the purpose of the administration, the manner of administration, and the like. A "therapeutically effective amount" is an amount sufficient to cure or ameliorate symptoms of CML.

The compounds of this may be delivered alone or in combination with other compounds used to treat CML. Such compounds include but are not limited to GLEEVEC, hydroxyurea, IFN-alpha, cytotoxic agents, 17-(Allylamino)-17-demethoxygeldanamycin or derivatives thereof, or wortmannin.

The compounds of this invention were prepared from: (a) commercially available starting materials (b) known starting materials which can be prepared as described in literature procedures or (c) new intermediates described in the schemes and experimental procedures herein. Compounds included in this invention can be prepared according to the synthesis routes disclosed in U.S. Pat. Nos. 6,002,008, and 6,780,996, such procedures are hereby incorporated by reference.

Reactions are performed in a solvent appropriate to the reagents and materials employed and suitable for the transformation being effected. It is understood by those skilled in the art of organic synthesis that the various functionalities present on the molecule must be consistent with the chemical transformations proposed. When not specified, order of synthetic steps, choice of protecting groups and deprotection conditions will be readily apparent to those skilled in the art. In addition, in some instances, substituents on the starting materials may be incompatible with certain reaction conditions. Restrictions pertinent to given substituents will be apparent to one skilled in the art. Reactions were run under inert atmospheres where appropriate.

The preparation of compounds of Formula I have been reported in the literature, [Boschelli, D. H., et. al., J. Med. Chem., 44, 3965 (2001)], Boschelli, D. H., et al., J. Med. Chem., 44, 822 (2001), Boschelli, D. H., et al., Bioorg. Med. Chem. Lett., 13, 3797 (2003), Boschelli, D. H., et. al., J. Med. Chem., 47, 1599 (2004), and Ye, F. et. al., 221th National Meeting of the American Chemical Society, San Diego, Calif. (April, 2001)].

The present invention further provides a compound of the invention for use as an active therapeutic substance for treating, preventing, or inhibiting CML in patients that have failed to respond to treatment with imatinib.

The present invention further provides a method of treating CML in humans patients that have failed to respond to treatment with imatinib, which comprises administering to the infected individual an effective amount of a compound or a pharmaceutical composition that is a substituted 3-cyanoquinoline. In one embodiment, the substituted 3-cyanoquinoline is SK606 (also known as SKI-606 or bosutinib. The chemical name for this compound is 4-[(2,4-Dichloro-5-methoxy-phenyl)amino]-6-methoxy-7-[3-(4-methyl-1-piperazinyl)propoxy]-3-quinolinecarbonitrile. The dose provided to a patient will vary depending upon what is being administered, the purpose of the administration, the manner of administration, and the like. A "therapeutically effective amount" is an amount sufficient to cure or ameliorate symptoms of CML. In one embodiment, the method for treating a BcrAbl positive leukemia in a subject that is resistant to imatinib comprises administering to the subject a therapeutically effective amount of 4-[(2,4-Dichloro-5-methoxy-phenyl)amino]-6-methoxy-7-[3-(4-methyl-1-piperazinyl)propoxy]-3-quinolinecarbonitrile, wherein the subject has at least one mutation in BcrAbl selected from M351T; F359V; H396P; I432T; F486S; M244V; L248V; G250E; Y253H; Y253F; E255K; K263E; L273M; T315I; F317L; and N331S.

The compounds of this may be delivered alone or in combination with other compounds used to treat CML. Such compounds include but are not limited to GLEEVEC, hydroxyurea, IFN-alpha cytotoxic agents, 17-(Allylamino)-17-demethoxygeldanamycin or derivatives thereof, or wortmannin.

The compounds of this invention and more particularly as described below in Examples 2 through 23 are or were prepared from: (a) commercially available starting materials (b) known starting materials which can be prepared as described in literature procedures or (c) new intermediates described in the schemes and experimental procedures herein. Compounds included in this invention can be prepared according to the synthesis routes disclosed in U.S. Pat. Nos. 6,002,008, and 6,780,996, such procedures are hereby incorporated by reference.

Example 1

Mutations known to be associated with resistance to imatinib are located in the bcr/abl gene are as follows, with the nucleotide position and the nucleotide change shown and followed in parentheses by the corresponding amino acid change shown in parentheses: 1052T>C (M351T); 1075T>K (F359V); 1187A>M (H396P); 1295T>Y (I432T); 1457T>C (F486S); 730A>G (M244V); 742C>S (L248V); 749G>R (G250E); 757T>C(Y253H); 758A>T (Y253F); 763G>R (E255K); 787A>R (K263E); 817T>A (L273M); 944C>T (T315I); 949T>C (F317L); and 992A>G(N331S).

Bone marrow aspirate samples were collected from subjects who failed imatinib treatment for Chronic Myeloid Leukemia, prior to dosing with SKI-606. The baseline bcr/abl gene was sequenced and point mutations were recorded. The patients were then dosed with SKI 606 and followed for best Cytogenetic and confirmed Hematological responses. Doses averaged between 400 mg and 600 mg per patient per day. It was confirmed that SKI-606 treatment resulted in cytogenetic or hematologic responses in patients harboring at least one of nineteen unique point mutations of the bcr/abl gene. These point mutations are associated with resistance to treatment with imatinib. Treatment times varied from one week to greater than a year.

Results of treatment of imatinib resistant human subjects having known BcrAbl resistance-associated mutations are shown in Table 1. A total of 66 patients resistant to imatinib were treated with SKI-606 for times varying between one week and more than one year per individual subject. Of these 66 patients, 42 had one or more mutations known to be associated with imatinib resistance. Furthermore, some patients not having one of the known resistance-associated mutations also responded favorably to treatment.

The following additional examples 2 through 23 describe compounds useful in the methods of the invention and are synthesized using (a) commercially available starting materials (b) known starting materials which can be prepared as described in literature procedures or (c) new intermediates described in the schemes and experimental procedures herein. Compounds included in this invention can be prepared according to the synthesis routes disclosed in U.S. Pat. Nos. 6,002,008, and 6,780,996, such procedures are hereby incorporated by reference.

TABLE 1

| Mutations | DNA | Protein | cytogenetic responders per subjects assessed | heme responders per subjects assessed | any responder per total subjects assessed | best cytogenetic response | best heme response |
|---|---|---|---|---|---|---|---|
| 1052T>C (M351T) | thymidine (T) to cytosine (C) | methionine to threonine | 3 out of 5 | 3 out of 4 | 4 out of 5 | 2-Ccyr, 1-Pcyr | 2-Complete heme response: 1-Accelerated to Chronic phase |
| 1075T>G (F359V) | thymidine (T) to guanine (G) | phenylalanine to valine | 1 out of 1 | 1 out of 2 | 1 out of 2 | 1-Ccyr | 1-Complete heme response |
| 1075T>K (F359[V,F]) | thymidine to thymidine or guanine | Phenylalanine to Phenylalanine and valine | 1 out of 2 | 2 out of 3 | 2 out of 3 | 1-Micyr | 1-Complete heme response: 1-Blast crisis to Chronic Phase |
| 1187A>M (H396(H,P) | Adenine (A) to A or C | histidine to histidine and phenylalanine | 1 out of 1 | 1 out of 1 | 1 out of 1 | 1-Ccyr | 1-Complete heme response |
| 1295T>Y (I432[T,I]) | T to T or C | isoleucine to isoleucine and threonine | 0 out of 1 | 1 out of 1 | 1 out of 1 | No Response | 1-Complete heme response |
| 1457T>C (F486S) | T to C | Phe to serine | 1 out of 2 | 1 out of 2 | 1 out of 2 | 1-Ccyr | 1-Blast crisis to Chronic Phase |
| 730A>G MUTATION (M244V) | A to G | met to valine | 1 out of 1 | Not Evaluable | 1 out of 1 | 1-Ccyr | Not Evaluable |
| 730A>R (M244[M,V]) | A to A or G | met to met and valine | Not Evaluable | 1 out of 1 | 1 out of 1 | Not Evaluable | Accelerated phase to Chronic phase |
| 742C>S (L248[L,V]) | C to C or G | Leucine to leu and valine | 0 out of 1 | 1 out of 1 | 1 out of 1 | No Response | 1-Complete heme response |
| 749G>R (G250{E,G}) | G to A or G | Glycine to glutamate and glycine | Not Evaluable | 1 out of 1 | 1 out of 1 | Not Evaluable | 1-Complete heme response |
| 757T>C (Y253{H,Y}) | T to C | tyrosine to tyrosine and histidine | 1 out of 1 | 1 out of 1 | 1 out of 1 | 1-Pcyr | 1-Complete heme response |
| 758A>T (Y253F) | A to T | tyrosine to phenylalanine | 0 out of 1 | 1 out of 1 | 1 out of 1 | No Response | 1-Complete heme response |
| 763G>R (E255[K,E]) | G to A or G | glutamate to glutamate and lysine | 1 out of 1 | 1 out of 1 | 1 out of 1 | 1-Pcyr, | 1-Blast crisis to Chronic Phase |
| 787A>R (K263[K,E]) | A to A or G | lysine to lysine and glutamate | Not Evaluable | 1 out of 1 | 1 out of 1 | Not Evaluable | 1-Complete heme response |

TABLE 1-continued

| Mutations | DNA | Protein | cytogenetic responders per subjects assessed | heme responders per subjects assessed | any responder per total subjects assessed | best cytogenetic response | best heme response |
|---|---|---|---|---|---|---|---|
| 817T>A (L273M) | T to A | Leucine to methionine | 1 out of 1 | 1 out of 1 | 1 out of 1 | 1-Ccyr | 1-Complete heme response |
| 944C>T (T315I) | C to T | threonine to isoleucine | | 1 out of 1 | 1 out of 6 | | 1-Complete heme response |
| 944C>Y (T315[T,I]) | C to C or T | threonine to threonine and isoleucine | 1 out of 1 | 0 out of 1 | 1 out of 1 | 1-Pcyr | No Response |
| 949T>C (F317L) | T to C | Phe to lysine | 1 out of 3 | 3 our of 4 | 3 out of 4 | 1-Micyr | 3-Complete heme response |
| 992A>C(N331S) | A to G | Asparagines to serine | 1 out of 1 | Not Evaluable | 1 out of 1 | 1-Ccyr | Not Evaluable |

Ccyr = Complete cytogenetic response
Pcyr = Partial cytogenetic response
MiCyr = Minimal cytogenetic response

Example 2

4-[(2,4-Dichloro-5-methoxyphenyl)amino]-6-methoxy-7-[3-(4-methyl-1-piperazinyl)propoxy]-3-quinolinecarbonitrile mp 116-120° C.; MS (ES) m/z 530.2, 532.2 (M+1).

Example 3

4-[(2,4-Dichloro-5-methoxyphenyl)amino]-7-[3-(4-ethyl-1-piperazinyl)propoxy]-6-methoxy-3-quinolinecarbonitrile; mp 102-104° C.; MS (ES) m/z 544.3, 546.4 (M+1).

Example 4

4-[(2,4-Dichloro-5-methoxyphenyl)amino]-6-methoxy-7-[2-(4-methyl-1-piperazinyl)ethoxy]-3-quinolinecarbonitrile mp 165-167° C.; MS (ES) m/z 516.0, 518.2 (M+1).

Example 5

4-[(2,4-Dichloro-5-methoxyphenyl)amino]-7-[2-(4-ethyl-1-piperazinyl)ethoxy-]-6-methoxy-3-quinolinecarbonitrile mp 101-105° C.; MS (ES) m/z 530.4, 532.4 (M+1).

Example 6

4-[(2,4-Dichloro-5-methoxyphenyl)amino]-6-methoxy-7-[(1-methylpiperidin-4-yl)methoxy]-3-quinolinecarbonitrile mp 200-202° C., MS 501.3 (M+H)+, Analysis for C.sub.25H.sub.26Cl.sub.2N.sub.4O.sub.3-0.8H.sub.2O, Calcd: C, 58.21; H, 5.39; N, 10.86. Found: C, 58.19; H, 5.23; N, 10.67.

Example 7

4-[(2,4-Dichloro-5-methoxyphenyl)amino]-6-methoxy-7-[2-(1-methylpiperidin-4-yl)ethoxy]-3-quinolinecarbonitrile mp 190-191° C., MS 515.9 (M+H)+, Analysis for C.sub.26H.sub.28Cl.sub.2N.sub.4O.sub.3-1.0H.sub.2O, Calcd: C, 58.53; H, 5.67; N, 10.50. Found: C, 58.65; H, 5.57; N, 10.34.

Example 8

4-[(2,4-Dichloro-5-methoxyphenyl)amino]-6-methoxy-7-[3-(1-methylpiperidin-4-yl)propoxy]quinoline-3-carbonitrile mp 144-145° C.; Mass spec. 529.2 (ES+).

Example 9

4-[(2,4-Dichloro-5-methoxyphenyl)amino]-7-[(1-ethylpiperidin-4-yl)methoxy]-6-methoxyquinoline-3-carbonitrile mp 192-195° C.; Mass spec. 515.2 (ES+).

Example 10

4-[(2,4-Dichloro-5-methoxyphenyl)amino]-6-ethoxy-7-[3-(4-methylpiperazin-1-yl)propoxy]quinoline-3-carbonitrile mp 137-138° C., MS 542.0 (M–H)–, Analysis for C.sub.27H.sub.31Cl.sub.2N.sub.5O.sub.3-0.6H.sub.2O, Calcd: C, 58.40; H, 5.84; N, 12.61. Found: C, 58.31; H, 5.71; N, 12.43.

Example 11

4-[(2,4-Dichloro-5-methoxyphenyl)amino]-6-ethoxy-7-[(1-methylpiperidin-4-y-l)methoxy]quinoline-3-carbonitrile mp 182-186° C., MS 513.0 (M–H)–, Analysis for C.sub.26H.sub.28Cl.sub.2N.sub.4O.sub.3-1.4H.sub.2OCalcd: C, 57.76; H, 5.74; N, 10.36. Found: C, 57.65; H, 5.43; N, 10.15.

Example 12

4-[(2,4-Dichloro-5-methoxyphenyl)amino]-6-ethoxy-7-[3-(4-ethylpiperazin-1-yl)propoxy]quinoline-3-carbonitrile mp 127-130° C., MS 558.3 (M+H)+, Analysis for C.sub.28H33Cl.sub.2N.sub.5O.sub.3-1.5H.sub.2O, Calcd: C, 57.44; H, 6.20; N, 11.96. Found: C, 57.44; H, 6.24; N, 11.79.

Example 13

4-[(2,4-Dichloro-5-methoxyphenyl)amino]-6-ethoxy-7-[3-(1-methylpiperidin-4-yl)propoxy]quinoline-3-carbonitrile mp 148-151° C. 543.2 (M+H)+, Analysis for C.sub.28H.sub.32Cl.sub.2N.sub.4O.sub.-3-1.8H.sub.2O, Calcd: C, 58.39; H, 6.23; N, 9.73. Found: C, 58.40; H, 6.16; N, 9.64.

Example 14

4-[(2,4-Dichloro-5-methoxyphenyl)amino]-6-ethoxy-7-[2-(4-methyl-1-piperazinyl)ethoxy]quinoline-3-carbonitrile mp 141-143° C., MS 530.2 (M+H)+, Analysis for C.sub.26H.sub.29Cl.sub.2N.sub.5O.sub.3, Calcd: C, 58.87; H, 5.51; N, 13.20. Found: C, 58.48; H, 5.45; N, 12.95.

Example 15

4-[(2,4-Dichloro-5-methoxyphenyl)amino]-6-ethoxy-7-[2-(1-methylpiperidin-4-yl)ethoxy]quinoline-3-carbonitrile mp 174-176° C., MS 529.1 (M+H)+, Analysis for C.sub.27H.sub.30Cl.sub.2N.sub.4O.sub.3, Calcd: C, 61.25; H, 5.71; N, 10.58. Found: C, 61.40; H, 5.84; N, 10.35.

Example 16

4-[(2,4-Dichloro-5-methoxyphenyl)amino]-6-methoxy-7-[3-(4-propyl-1-piperazinyl)propoxy]-3-quinolinecarbonitrile 1° C.; MS (ES) m/z 558.2, 560.2 (M+1).

Example 17

4-[(2,4-dichlorophenyl)amino]-6-methoxy-7-[(1-methylpiperidin-4-yl)methoxy-]-3-quinolinecarbonitrile mp 224-225° C., MS 469.0 (ES−).

Example 18

6-methoxy-7-[(1-methylpiperidin-4-yl)methoxy]-4-[(3,4,5-trimethoxyphenyl)amino]quinoline-3-carbonitrile mp>245° C.; HRMS (M+H)+calculated 493.24455, found 493.24311.

Example 19

4-[(2-chloro-5-methoxyphenyl)amino]-6-methoxy-7-[(1-methylpiperidin-4-yl)m-ethoxy]quinoline-3-carbonitrile mp 106-108° C., MS 467.2 (ES+).

Example 20

6-methoxy-4-[(5-methoxy-2-methylphenyl)amino]-7-[(1-methylpiperidin-4-yl)m-ethoxy]quinoline-3-carbonitrile mp>250° C., MS 445.2 (ES−).

Example 21

4-[(2,4-dimethylphenyl)amino]-6-methoxy-7-[(1-methylpiperidin-4-yl)methoxy-]quinoline-3-carbonitrile mp 190-191° C., MS 429.2 (ES−).

Example 22

6-methoxy-4-[(5-methoxy-2,4-dimethylphenyl)amino]-7-[(1-methylpiperidin-4-yl)methoxy]quinoline-3-carbonitrile mp 160-162° C., MS 461.3 (ES+).

Example 23

4-[(2,4-dichloro-5-ethoxyphenyl)amino]-6-methoxy-7-[(1-methylpiperidin-4-y-l)methoxy]quinoline-3-carbonitrile.

Example 24

A group of human patients suffering from a BcrAbl positive leukemia and resistant to treatment with imatinib were treated with SKI-606 for time periods ranging between one week and more than one year.

FIG. 1 shows the hematologic and cytogenetic response for patients by number (N) and % and differentiated between chronic and advanced leukemia.

FIG. 2 shows the median bcrabl to abl gene expression ratio in chronic phase imatinib resistant patients treated with SKI-606.

Example 25

Table 2 represents follow on data collected for additional responders to the mutations described above in Table 1 as well as responders and non-responders to additional bcrabl mutations.

TABLE 2

| Mutations | cytogenetic responders per subjects assessed | heme responders per subjects assessed | cytogenetic responders per subjects assessed as per TABLE 1 | heme responders per subjects assessed as per TABLE 1 |
| --- | --- | --- | --- | --- |
| M351T | 4 out of 6 | 5 out of 5 | 3 out of 5 | 3 out of 4 |
| F359V | 3 out of 4 | 5 out of 5 | 2 out of 3 | 3 out of 5 |
| H396P | 1 out of 1 | 1 out of 1 | 1 out of 1 | 1 out of 1 |
| I432T | 0 out of 1 | 1 out of 1 | 0 out of 1 | 1 out of 1 |
| F486S | 1 out of 2 | 1 out of 2 | 1 out of 2 | 1 out of 2 |
| M244V | 4 out of 4 | 4 out of 4 | 1 out of 1 | 1 out of 1 |
| L248V | 1 out of 3 | 2 out of 2 | 0 out of 1 | 1 out of 1 |
| G250E | 0 out of 1 | 2 out of 2 | Not Evaluable | 1 out of 1 |
| Y253{H, F} | 3 out of 3 | 3 out of 3 | 1 out of 2 | 2 out of 2 |
| E255K | 2 out of 2 | 2 out of 3 | 1 out of 1 | 1 out of 1 |
| K263E | 1 out of 1 | 1 out of 1 | Not Evaluable | 1 out of 1 |
| T315I | 3 out of 3 | 5 out of 9 | 1 out of 1 | 1 out of 2 |
| F317L | 1 out of 6 | 7 out of 8 | 1 out of 3 | 3 our of 4 |
| N331S | 1 out of 1 | Not Evaluable | 1 out of 1 | Not Evaluable |
| L384P | 0 out of 1 | 0 out of 1 | | |
| V299L | 0 out of 1 | 0 out of 1 | | |
| E453K | 1 out of 1 | 1 out of 1 | | |
| F359I | 1 out of 1 | 1 out of 1 | | |
| E355G | 0 out of 1 | 1 out of 1 | | |
| G321R | 0 out of 1 | 1 out of 1 | | |

TABLE 2-continued

| Mutations | cytogenetic responders per subjects assessed | heme responders per subjects assessed | cytogenetic responders per subjects assessed as per TABLE 1 | heme responders per subjects assessed as per TABLE 1 |
|---|---|---|---|---|
| H396R | 0 out of 2 | 1 out of 1 | | |
| F311L | Not Evaluable | Not Evaluable | | |
| E255V | Not Evaluable | 1 out of 2 | | |
| L273M | 1 out of 1 | 1 out of 1 | 1 out of 1 | 1 out of 1 |
| T277A | 1 out of 1 | 1 out of 1 | | |
| E286G | 1 out of 1 | 1 out of 1 | | |
| L387V | 0 out of 1 | 1 out of 1 | | |
| Q252H | Not Evaluable | Not Evaluable | | |
| Y230H | 0 out of 1 | 1 out of 1 | | |

The invention claimed is:

1. A method for treating a BcrAbl positive leukemia in a subject that is resistant to imatinib which comprises administering to the subject a therapeutically effective amount of 4-[(2,4-Dichloro-5-methoxy-phenyl)amino]-6-methoxy-7-[3-(4-methyl-1-piperazinyl)propoxy]-3-quinolinecarbonitrile, wherein the subject has a mutation in BcrAbl protein at F317L.

2. A method for treating a BcrAbl positive leukemia in a subject that is resistant to imatinib which comprises administering to the subject a therapeutically effective amount of 4-[(2,4-Dichloro-5-methoxy-phenyl)amino]-6-methoxy-7-[3-(4-methyl-1-piperazinyl)propoxy]-3-quinolinecarbonitrile, wherein the subject has a resistance-associated nucleic acid mutation in the BcrAbl gene at 949T>C.

3. The method of claim 1, wherein the leukemia is Chronic Myelogenous Leukemia.

4. The method of claim 2, wherein the leukemia is Chronic Myelogenous Leukemia.

5. The method of claim 1, wherein the leukemia is Acute Lymphocytic Leukemia.

6. The method of claim 2, wherein the leukemia is Acute Lymphocytic Leukemia.

7. The method of claim 1, wherein the compounds are administered to the subject in combination with one or more other compounds used to treat a BcrAbl positive leukemia.

8. The method of claim 2, wherein the compounds are administered to the subject in combination with one or more other compounds used to treat a BcrAbl positive leukemia.

9. The method of claim 7, wherein the one or more other compounds includes imatinib.

10. The method of claim 8, wherein the one or more other compounds includes imatinib.

* * * * *